(12) United States Patent
Gunn et al.

(10) Patent No.: US 9,603,632 B1
(45) Date of Patent: Mar. 28, 2017

(54) TULIP BONE SCREW ASSEMBLY

(71) Applicant: Amendia, Inc., Marietta, GA (US)

(72) Inventors: Joshua David Gunn, Woodstock, GA (US); David Brett Cain, Marietta, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 15/159,912

(22) Filed: May 20, 2016

(51) Int. Cl.
*A61B 17/70* (2006.01)
*A61B 17/00* (2006.01)
*A61B 17/86* (2006.01)

(52) U.S. Cl.
CPC ...... *A61B 17/7037* (2013.01); *A61B 17/7032* (2013.01); *A61B 17/8635* (2013.01); *A61B 2017/00526* (2013.01)

(58) Field of Classification Search
CPC ............ A61B 17/7032; A61B 17/8635; A61B 17/7037; A61B 2017/00526
USPC ........ 606/246, 264–270, 272, 279, 305, 308
See application file for complete search history.

(56) References Cited

U.S. PATENT DOCUMENTS

| | | |
|---|---|---|
| 5,964,760 A | 10/1999 | Richelsoph |
| 7,087,057 B2 | 8/2006 | Konieczynski et al. |
| 7,927,360 B2 | 4/2011 | Pond et al. |
| 7,942,911 B2 | 5/2011 | Doubler et al. |
| 8,377,101 B2 | 2/2013 | Barrus et al. |
| 8,465,530 B2 | 6/2013 | Hammill et al. |
| 8,858,605 B1 | 10/2014 | Glatzer et al. |
| 9,155,568 B2 | 10/2015 | Biedermann et al. |
| 9,155,579 B2 | 10/2015 | Konieczynski et al. |
| 9,289,246 B2 | 3/2016 | Biedermann et al. |
| 2015/0209085 A1* | 7/2015 | Biedermann ...... A61B 17/7034 606/266 |

\* cited by examiner

*Primary Examiner* — Pedro Philogene
*Assistant Examiner* — David C Comstock
(74) *Attorney, Agent, or Firm* — David L. King

(57) ABSTRACT

A tulip bone screw assembly has a bone screw, a tulip and a saddle. The bone screw has a threaded shank and a polyaxial head. The tulip has a slotted opening for receiving a rod and an open distal end for passing the shank of the bone screw and holding the head and a locking ring positioned between the slotted opening and the distal end. The saddle has an axis defined by a center opening, a proximal concave end for engaging and holding the rod and a distal end with a plurality of friction fingers bent inwardly toward an axis of the saddle for applying a friction force to the head of the bone screw.

18 Claims, 12 Drawing Sheets

US 9,603,632 B1

TULIP BONE SCREW ASSEMBLY

TECHNICAL FIELD

The present disclosure relates to a bone screw system. More specifically, a bone screw system with an improved bone screw positioning feature for use in spinal surgery is presented.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

Those bone screw connectors often employ tabs or towers to facilitate the assembly. Once the screws and rods are fixed in place, these tabs or towers are removed from the connector. Various means to remove the tabs have been used including releasable pins and frangible tear or fracture seams. The tabs or towers often called extension legs vary in length from short, an inch or less, to very long, four or more inches. The removal of these extension legs needs to be simple and reliable. Most preferably, the removal needs to be consistent. The attachment must be secure so as not to prematurely fail, but not so strong as to require large forces or multiple flexing to release the legs. Some prior art bone screws have resorted to separate tools to initiate a breakage of a connection due in part to the excessive forces required, as taught in U.S. Pat. No. 7,927,360.

In U.S. Pat. No. 8,858,605, a prior art bone screw system is disclosed that has a fixation element, a receiving element, coupling element, and a compression element. The fixation element was a screw. The receiving element defined an internal bore sized to receive the shank portion of the fixation element and had a seat adapted to support the head portion of the fixation element. The seat of the receiving element was shaped to substantially conform to an exterior portion of the head portion of the fixation element. In this prior art patent, the systems functional features are described as follows.

The receiving element was further adapted to receive a stabilizer rod. As such, in one aspect, the receiving element comprised a pair of opposed legs separated by a rod-receiving channel. This created a defined shape often referred to as a tulip in the orthopedic fastener art.

In another aspect, the bone screw system also comprised a pair of leg extensions. Each leg extension had a first end and a second end, where the second end was coupled to a respective opposed leg of the receiving element.

The compression element was engageable with the receiving element. In one aspect, the compression element was adapted to move downward into the compression element receiving chamber to translate a force to the stabilizer rod and translate a force onto the head portion of the fixation element and substantially fix the position of the fixation element with respect to the receiving element.

In one embodiment, a breakaway groove was positioned externally on each leg or leg extension. The breakaway groove extended inwardly at least partially through the wall of each leg or leg extension. This created an aperture or slit in the wall leaving the wall with at least one, preferably a pair of leg attachments connecting each leg to each respective leg extension adjacent the aperture.

In a preferred embodiment, the leg extensions also had threads continuing from the legs along its length at distances equal or less than the length of the leg extension. The threads accepted the external threads of the compression element. The wall thickness of the legs or leg extension was a minimum (t) at the thread groove and the breakaway groove extended to at least a portion of a thread groove at the distance of (t) or greater. The internal threads of the legs and leg extensions had a pitch so the threads formed a helix angle and the breakaway groove intersected the pitch along at least one thread or thread groove.

The breakaway groove was oriented perpendicular to an axis of the receiving channel.

All of these early systems had an undesirable feature that although allowed the bone screw to be polyaxial relative to the connector, it freely moved or flopped about on insertion making it hard to control. The present invention solves this issue and affords the surgeon a much easier to use bone screw system assembly.

These and other objectives are achieved by the invention as described hereinafter.

SUMMARY OF THE INVENTION

A tulip bone screw assembly has a bone screw, a tulip and a saddle. The bone screw has a threaded shank and a polyaxial head. The tulip has a slotted opening for receiving a rod and an open distal end for passing the shank of the bone screw and holding the head and projections positioned between the interior threads of the tulip and the distal end. The saddle has an axis defined by a center opening, a proximal concave end for engaging and holding the rod and a distal end with a plurality of friction fingers bent inwardly toward an axis of the saddle for applying a friction force to the head of the bone screw. The saddle having an exterior locking surface or groove positioned between the ends, the locking surface or groove being sized to move axially inside the tulip past the projections fixing the saddle inside the tulip on insertion. The head of the bone screw is spaced between the distal end and the friction fingers on assembly wherein the head is sized to bend the friction fingers outwardly creating a friction force to hold the screw position relative to the axis of the tulip.

The head of the bone screw has an at least partially hemispherical or spherical shape. The head of the bone screw also has a driving feature for torsionally driving the bone screw into bone. The driving feature can be a hexagonal or star shape opening for receiving a torque driver. The plurality of friction fingers are integral to a saddle body. In one embodiment, the tulip has a recess adjacent the distal end, the recess of the tulip is configured to receive a plurality of arcuate locking ring segments. The combined outer diameter of the locking ring segments is larger than a distal opening of the tulip at the distal end.

The bone screw has one of the following head shapes; at least partially a hemispherical or spherical head, conical or a radial array or loci of cylindrical surfaces or any other bulbous head.

A method of assembling a tulip has the steps of providing a tulip with projections; and positioning a saddle with a concave locking surface or groove inside the tulip over the projections inside the tulip in pre-loaded first position. The method of assembling a tulip also includes the steps of inserting the head of the bone screw bottom loading the bone screw into the tulip to create the assembly and inserting the plurality of arcuate locking segments to fix the bone screw and then re-positioning the saddle by pushing the concave locking surface or groove past the projections inside the tulip to a second position.

The method of assembling a tulip can include the step of inserting the locking segments into the tulip and pushing the bone screw head bending the friction fingers on assembly to create a friction force to position a shank of the bone screw.

In a preferred embodiment, a rod receiving bone screw assembly has a bone screw, a tulip and a plurality of arcuate locking segments and a saddle. The bone screw has a threaded shank and polyaxial spherical head. The tulip has a slotted opening for receiving a rod and internal threads inside the tulip and projections below the internal threads. The plurality of arcuate locking segments internal of the tulip positioned in a recess of an inner surface of the tulip. The saddle has an axis defined by a center opening, a proximal concave end for engaging and holding the rod and a distal end with a plurality of friction fingers bent toward an axis of the saddle for applying a friction force to the head of the bone screw. The saddle has an exterior locking surface positioned between the ends of the saddle. The locking surface or groove is sized to move axially inside the tulip onto the projections fixing the saddle inside the tulip on insertion and after insertion of the saddle into the tulip forming the rod receiving bone screw assembly, the bone screw is positioned wherein a lower surface of the bone screw head rests against the locking ring segments in a pre-assembled unfixed position, the saddle is then moved further inwardly with the proximal end of the saddle past the projections causing the bone screw to be positioned wherein the friction fingers move proximally pressing the head of the bone screw against the locking segments causing the bone screw shank to be held frictionally but adjustably movable relative to the axis of the saddle prior to rod insertion locking the bone screw into the tulip.

BRIEF DESCRIPTION OF THE DRAWINGS

The invention will be described by way of example and with reference to the accompanying drawings in which.

DETAILED DESCRIPTION OF THE INVENTION

Figure 1:
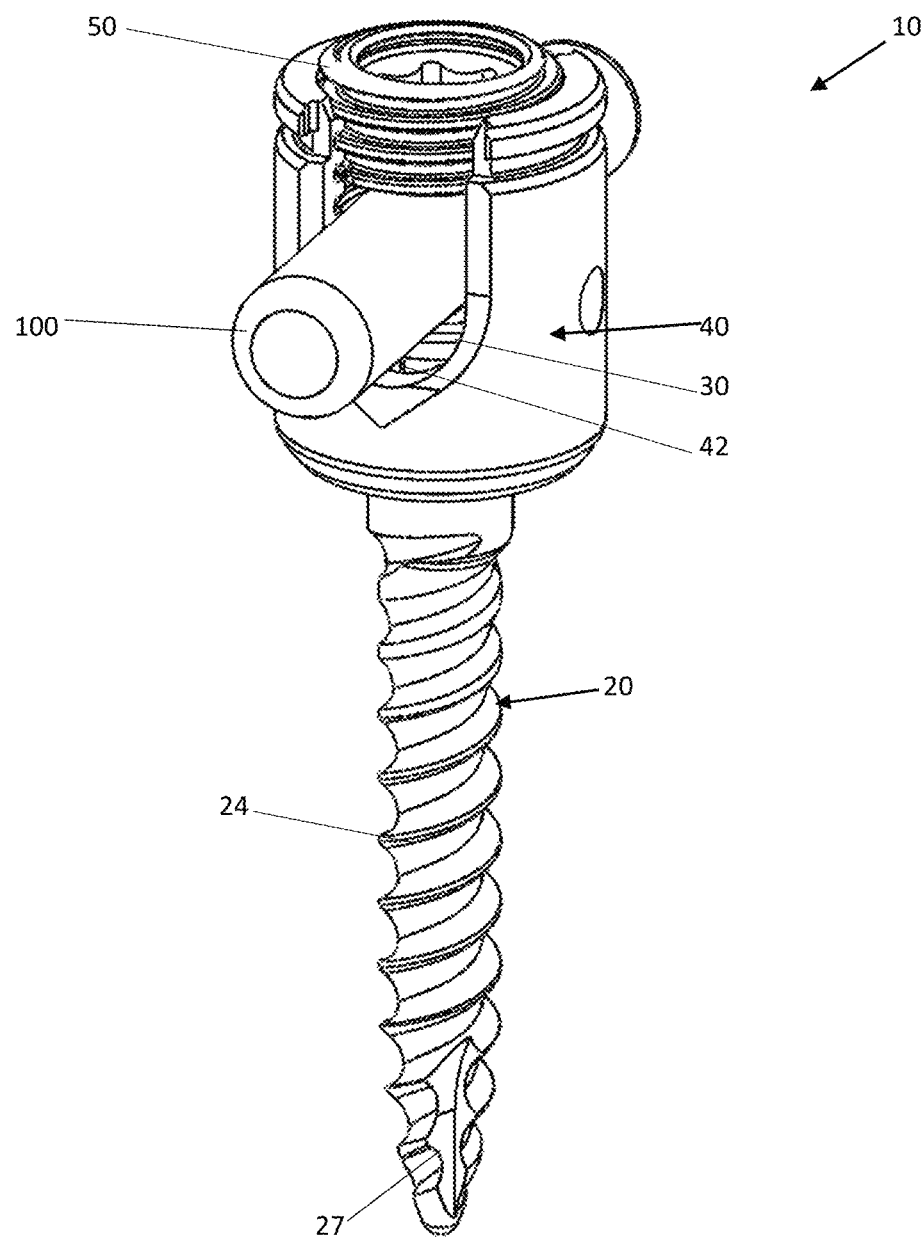
FIG. 1 is a perspective view of the tulip bone screw assembly of the present invention illustrating a rod and set screw inserted into a tulip.

With reference to FIG. 1, a tulip bone screw assembly 10 is illustrated. As shown, the tulip bone screw assembly 10 has a fixation rod 100 shown positioned between a slotted opening 42 held in place by a set screw 50 threadingly engaged to internal threads 46 inside the tulip. The set screw 50, when firmly positioned against the rod 100 presses against a saddle 30 thereby fixing the rod 100 firmly in place inside the tulip 40. Below the saddle 30 a bone screw 20 is shown extending through an opening 44 in the tulip 40. The bone screw 20 has the threaded portion 24 extending to a distal end tip as shown with cutting flutes 27 for cutting into bone on insertion.

Figure 2:
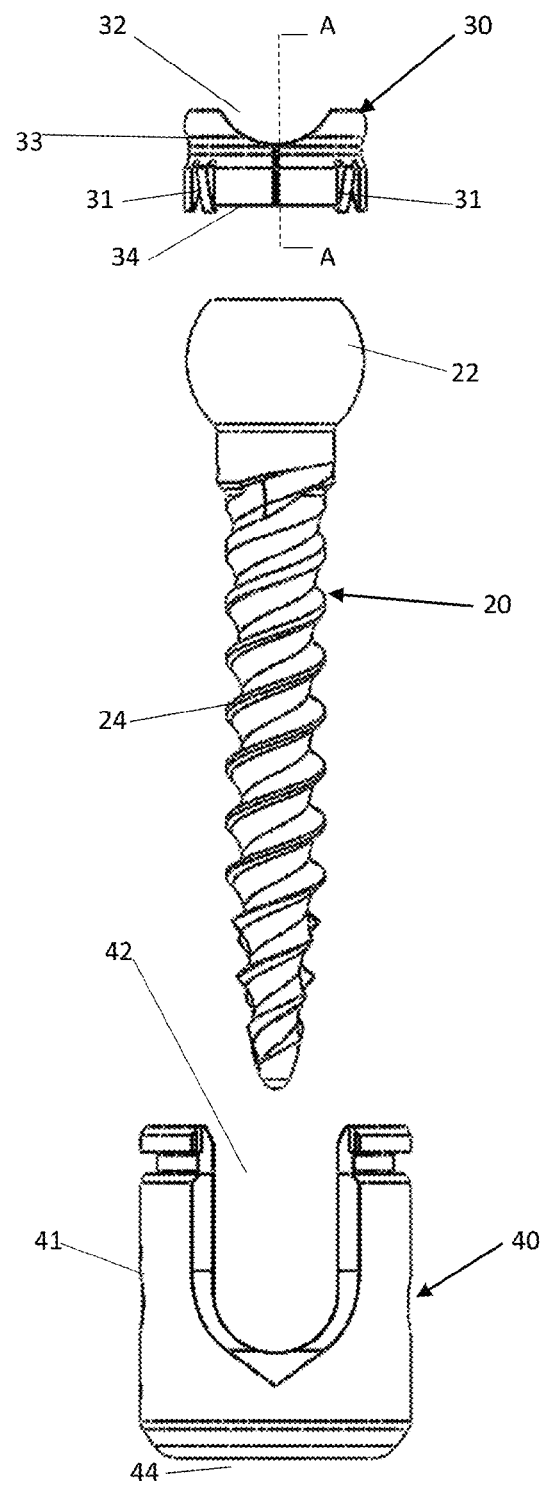
FIG. 2 is an exploded plan view of the tulip bone screw assembly of the present invention from FIG. 1 without the rod and set screw.

With reference to FIG. 2, the tulip bone screw assembly 10 is shown in an exploded view with the rod 100 and set screw 50 removed. As illustrated in this first embodiment of the invention, the screw 20 has a threaded shank 24 extending from the distal end to a proximal end having an enlarged bulbous head 22. Above the screw 20 is illustrated the saddle 30, as shown the saddle 30 has a concave recess 32 for receiving the rod. This concave recess 32 is sized so that the rod 100 can fit in the bottom of the concave recess 32 and be snugly positioned therein on assembly. The saddle 30 has an interior surface 34 for receiving the head 22 of the bone screw 20. As illustrated, there are a plurality of friction fingers 31. These friction fingers 31 are bent inwardly towards the axis A of the saddle 30. This inward bending of the friction fingers 31 allows the saddle on assembly to first engage an exterior upper surface of the bulbous head 22. As shown, the bulbous head 22 is at least partially hemispherical or spherical in shape such that when the friction fingers 31 make contact with the exterior surface it provides a force on that surface during assembly. The saddle 30 further has a locking groove 33 as illustrated. The locking groove or surface 33 is positioned between the proximal and distal ends of the saddle. The locking surface 33 is sized to move axially inside the tulip 40 on assembly. The lower portion of FIG. 2 illustrates the tulip 40. The tulip 40 as illustrated, has a channeled slot or opening 42 for receiving a rod 100 and a distal opening 44 allowing the threaded shank 24 of bone screw 20 to pass through. In some embodiments the bulbous head 22 is smaller than the threaded shank 24 and in such case the bulbous head 22 will pass through a bottom approach into the opening 44. In other cases when the threaded shank 24 is smaller than the opening 44, the bone screw can simply be inserted from the top and pass through the opening 44 toward an end 45 wherein the bone screw 20 will approach the distal end 45 and will be held at the bulbous head 22 by a conical or tapered surface 48.

Figure 2A:
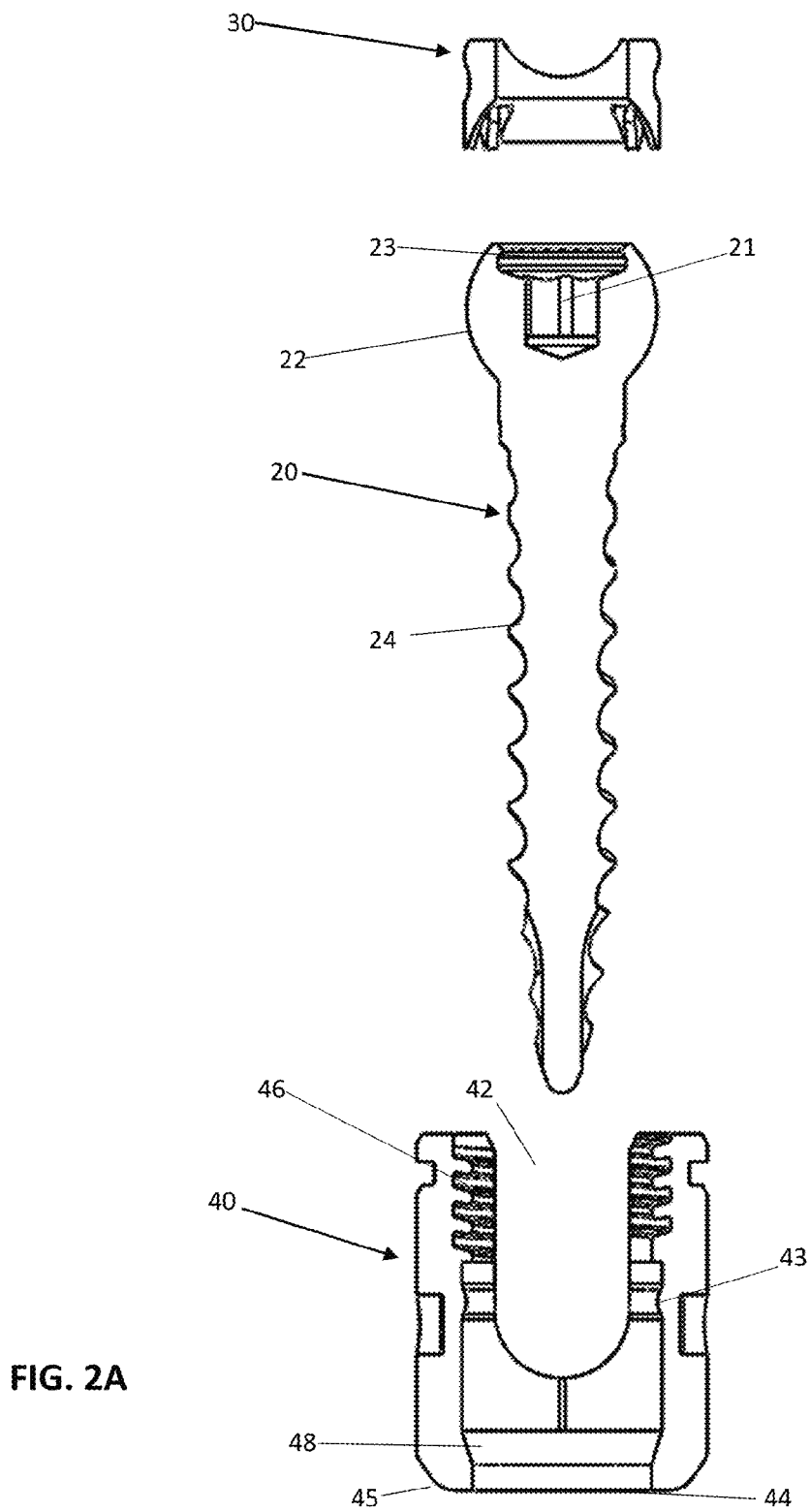
FIG. 2A is the view of FIG. 2 shown in cross-section of a first embodiment of the invention.
Figure 3:
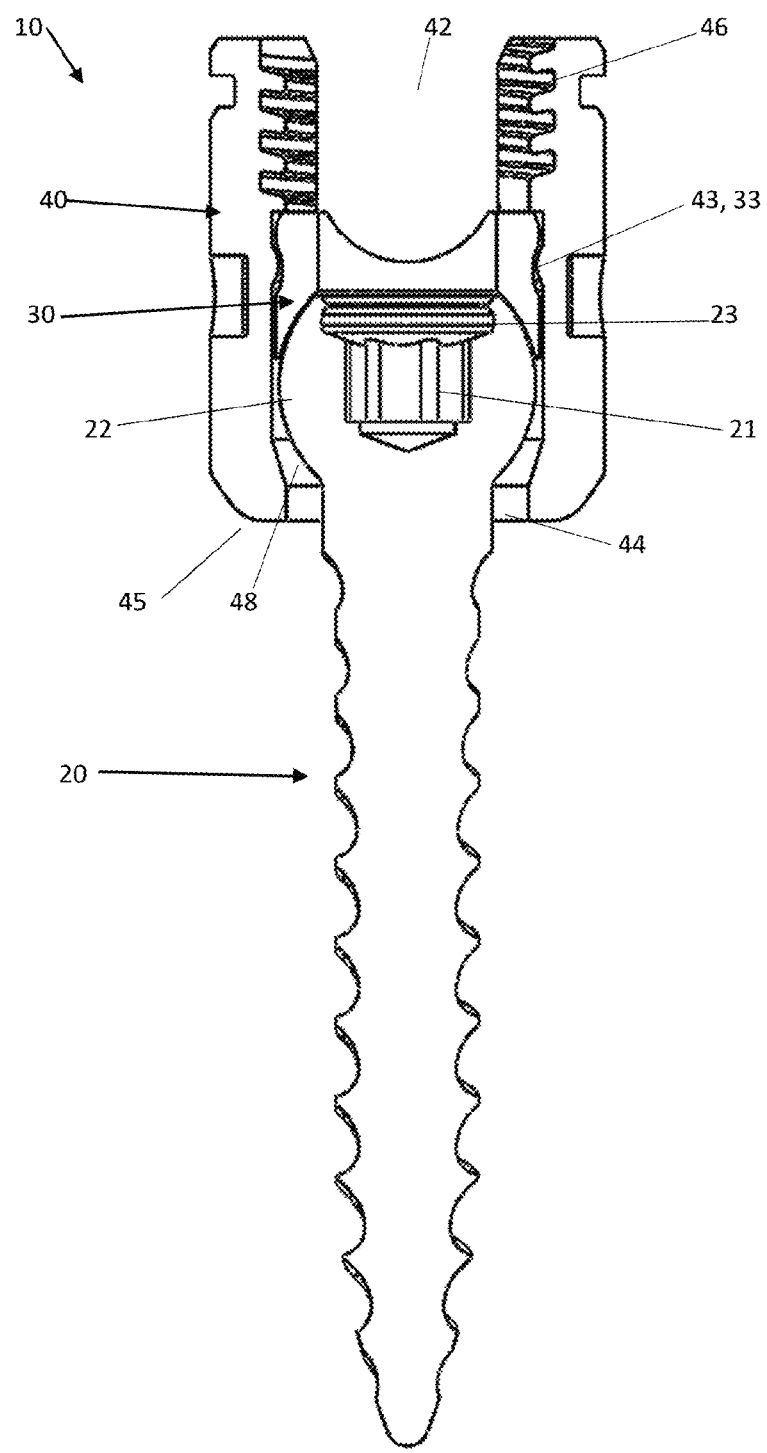
FIG. 3 is a cross-sectional view of the first embodiment of FIG. 2A with the bone screw shown with the saddle in a pre-loaded assembly position.

With reference to FIG. 2A, a cross-sectional view shows the saddle 30, the bone screw 20 and the tulip 40. As shown in FIGS. 2A and 3, the tulip 40 has a distal end 45 shown at the opening 44 wherein the distal end 45 has a tapered surface 48. This tapered surface 48 is smaller than the bulbous head 22 of the bone screw 20, as illustrated in this first embodiment. As such, the bone screw 20 on assembly passes through top of the tulip 40 inwardly until it rests on the tapered surface 48. With reference to FIG. 3, the saddle 30 is shown moved into a pre-loading position, as such, the head 22 of the bone screw 20 in contact with the saddle 30. The saddle 30 has a recess groove or surface 33 that will pass onto projections 43. On assembly, an interference fit is created with the exterior surface of the saddle 30 such that the saddle 30 can be pushed inwardly to this first position wherein the recess 33 is engaged with the projections 43. The force required for this initial contact is approximately 150 lbs to position the saddle 30 in this first location. As shown, the projections 43 are formed as two arcuate projections.

Figure 4:
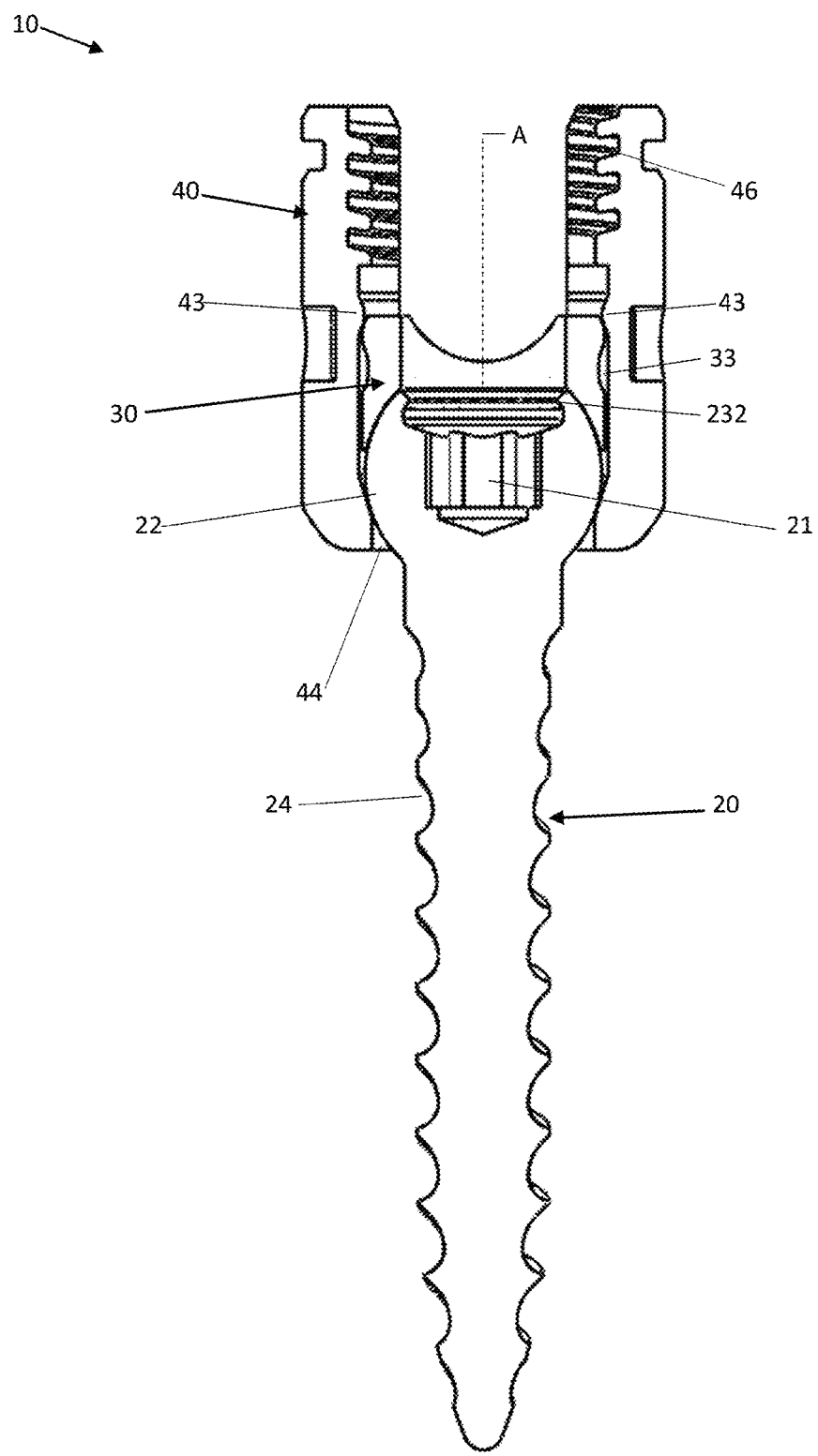
FIG. 4 is a second cross-sectional view showing the saddle moved in a final assembly position.

With reference to FIG. 4, on final assembly with the bone screw 20 in position loose as in FIG. 3, a press force can be applied such that the saddle 30 is moved past the projections 43 such that the recess 33 is positioned below the projections 43 and held in position in this final assembly position. At this point, the head of the bone screw 22 is firmly positioned between the tulip's distal end 45 along the tapered surface 48 as illustrated and firmly engaged against the inner surface 34 of the saddle 30. A force of approximately 230 lbs is required to move the saddle 30 firmly engaged against the upper exterior surface of the head 22 of the bone screw 20 and past the projections 43. This force is sufficient to cause the plurality of friction fingers 31 to deflect outwardly back to the shape mimicking the contour of the exterior surface of the head 22 of the bone screw 20. Since these friction fingers 31 in the deflected condition are applying a force on the exterior surface of the head 22 of the bone screw 20. The bone screw 20 is effectively locked in position. It is believed preferable that a plurality of such friction fingers 31 be used, most preferably at least 3, so that the head 22 of the bone screw 20 can be firmly positioned such that it will not freely move absent being physically adjusted. As shown, four fingers 31 are provided. This feature is quite important to the surgeon as it allows him to direct the tip of the bone screw 20 precisely on implantation such that the tip will be oriented directionally where the surgeon wants to initiate threading the screw 20 into the bone. This is important because in past inventions, the polyaxial bone screw when placed in such a tulip would freely move and as such the surgeon could not control the tip location absent an extra component. As shown, the bone screw 20 has threads 23 inside the head 22 area shown as a cutaway. The threads 23 allow a tool to be provided for engaging the bone screw 20. In addition a torque driving opening 21 is illustrated, as shown, this can be a star recess configuration, or a hexagonal configuration or any shape where a torque driving instrument can be provided to fasten the screw into the bone. This entire assembly 10, as shown in FIG. 4 of this first embodiment, is how the bone screw will be received when the surgeon takes the assembly out for implantation. As shown, the bone screw 20 is positioned such that the longitudinal axis of the shank of the bone screw 20 is co-aligned with the axis A of the saddle. When the surgeon goes to use the tulip bone screw assembly 10, he can simply move the shank directionally out of alignment to any angle he wants within the range of the polyaxial movement of the head 22. Due to the fact that the friction fingers 31 are applying force, the screw will stay in this position until physically moved.

Figure 5:
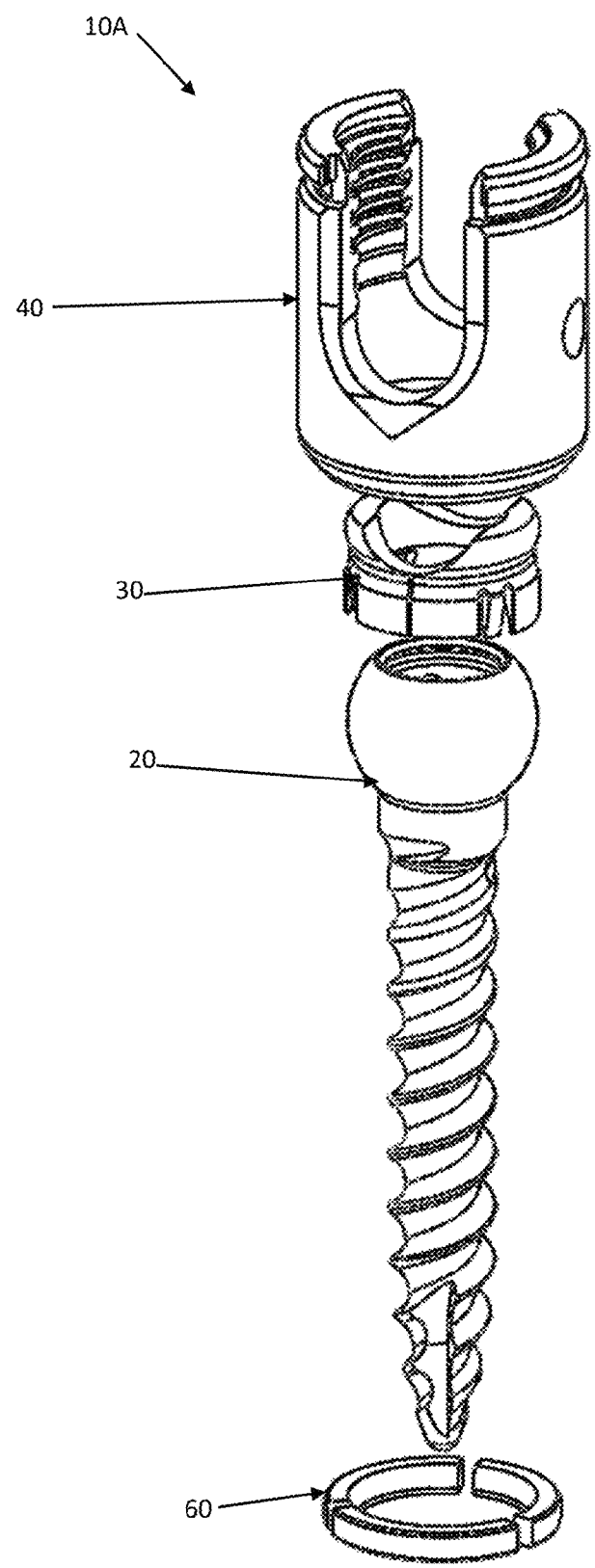
FIG. 5 shows a perspective of a second embodiment made in accordance with the present invention shown without the rod or set screw.
Figure 5A:
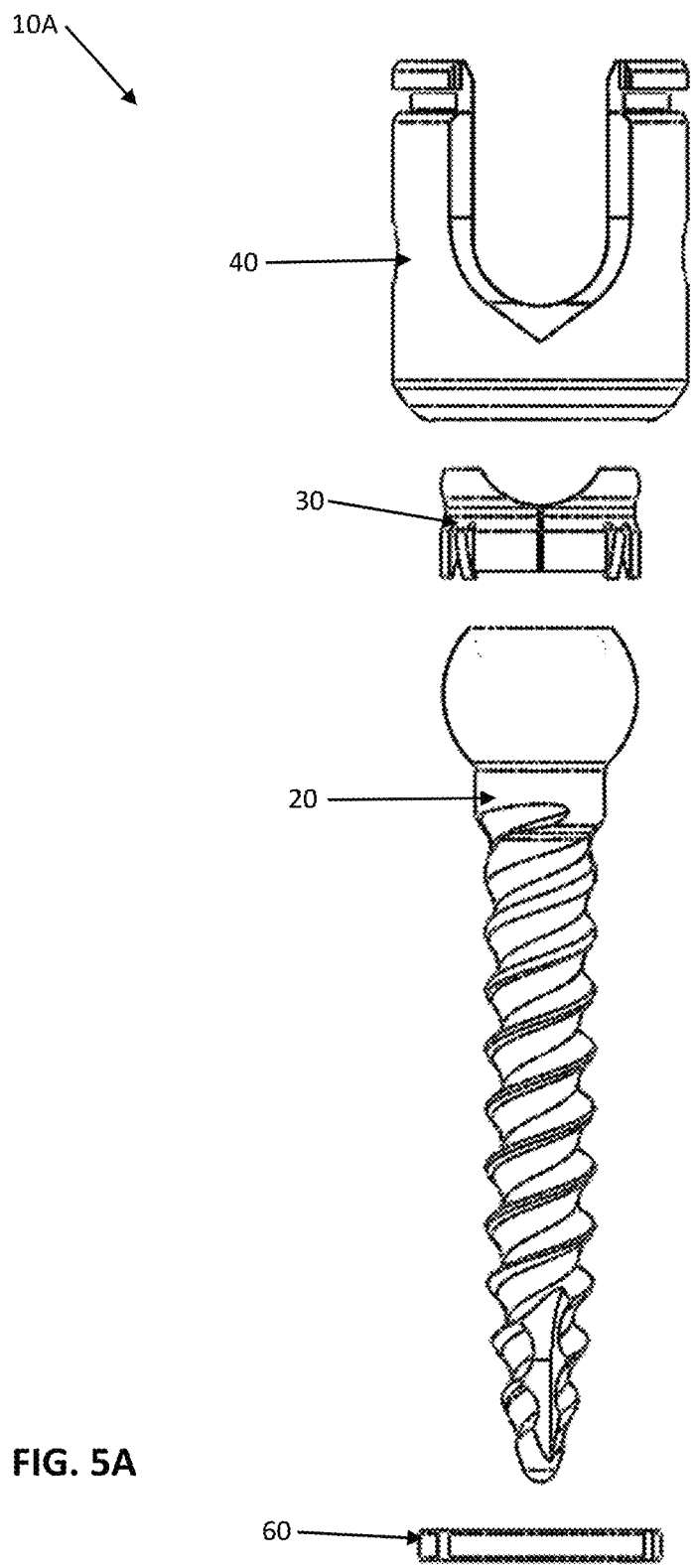
FIG. 5A is a plan view of the second embodiment of FIG. 5.
Figure 5B:
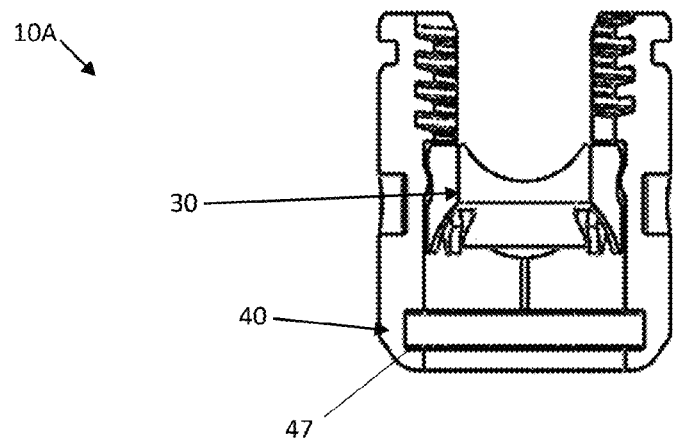
FIG. 5B is a cross-sectional view of the present invention as shown in figure 5A.
Figure 5B:
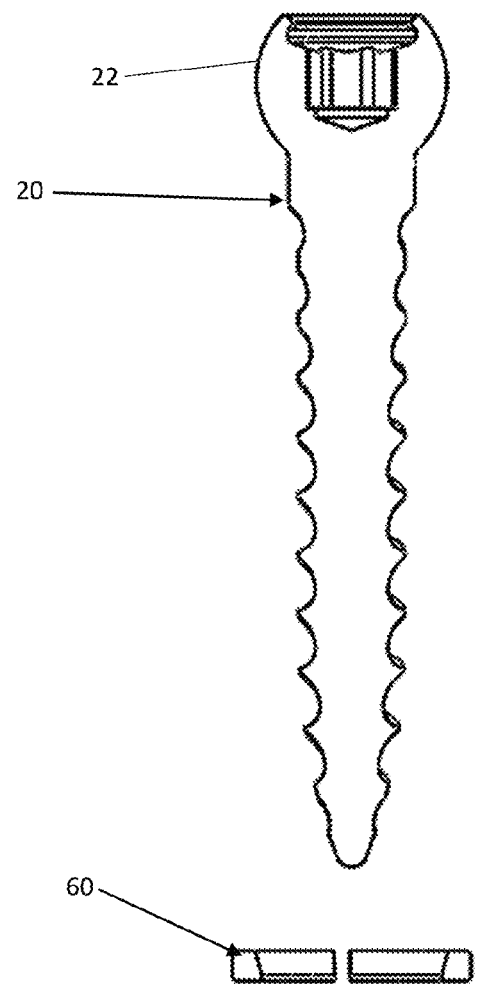
Figure 5C:
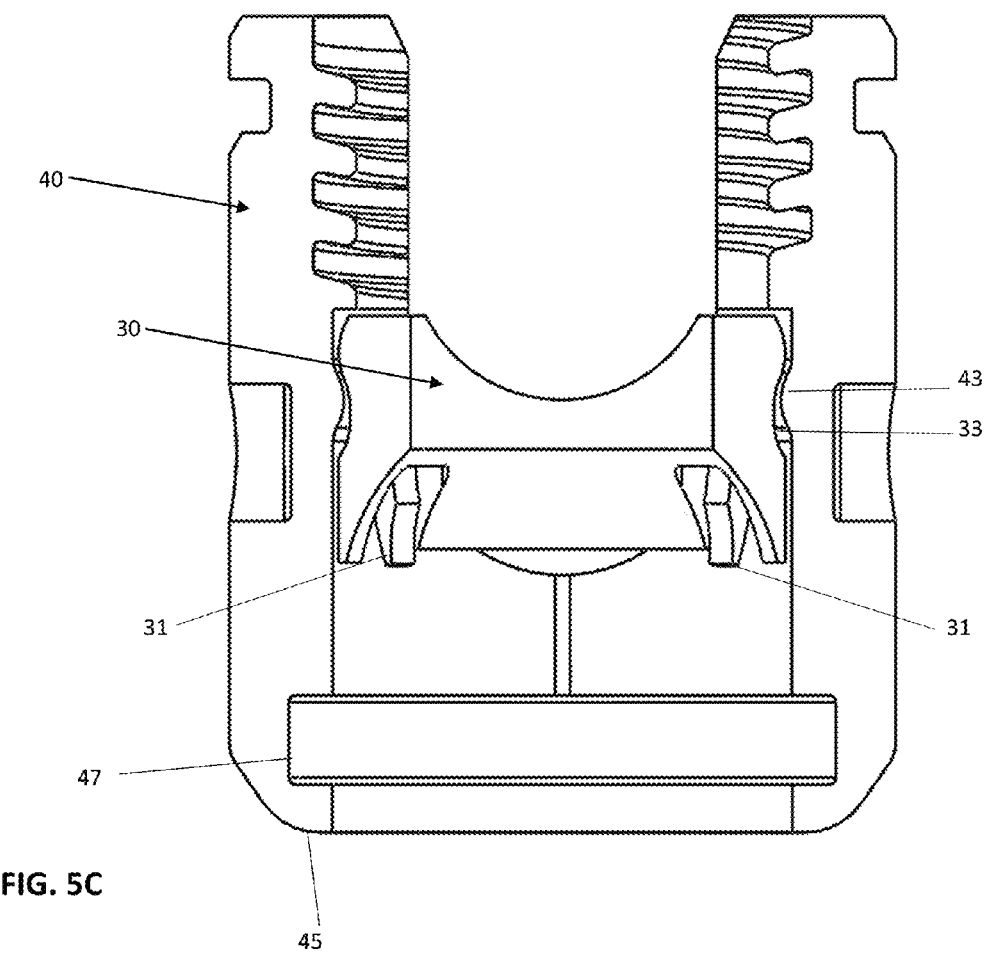
FIG. 5C is an enlarged cross-sectional view of the tulip and saddle of the second embodiment assembled in a pre-loaded position.

With reference to FIG. 5, a second embodiment of the invention is shown. In this embodiment, hereinafter called 10A, the same tulip 40, saddle 30 and bone screw 20 are employed with a modification to the tulip 40 such that a plurality of arcuate locking segments when axially aligned to a center form a locking ring assembly 60, as illustrated, can be used. A plan view of this assembly 10A is shown in FIG. 5A, all the features as previously discussed are the same generally with the exception of how the bone screw 20 can be assembled. As shown in FIG. 5B a cross-sectional view of this assembly 10A is illustrated. The assembly 10A has a recess channel cut into the tulip 40 towards the distal end 45. This recess 47 is sized such that the locking ring assembly 60 can positioned inside this recess or groove 47. As such the locking ring assembly 60 will protrude inwardly from the interior surface of the tulip 40 in such a way that it will provide a smaller assembled inside diameter than the head 22 of the bone screw 20. With reference to FIG. 5C, one can see the saddle 30 in the initial pre-assembly position wherein the saddle 30 shows the friction fingers 31 bent inwardly as previously described and as shown the recess surface or groove 33 is positioned over the projections 43 of the tulip 40. This is a pre-assembly position.

Figure 6:
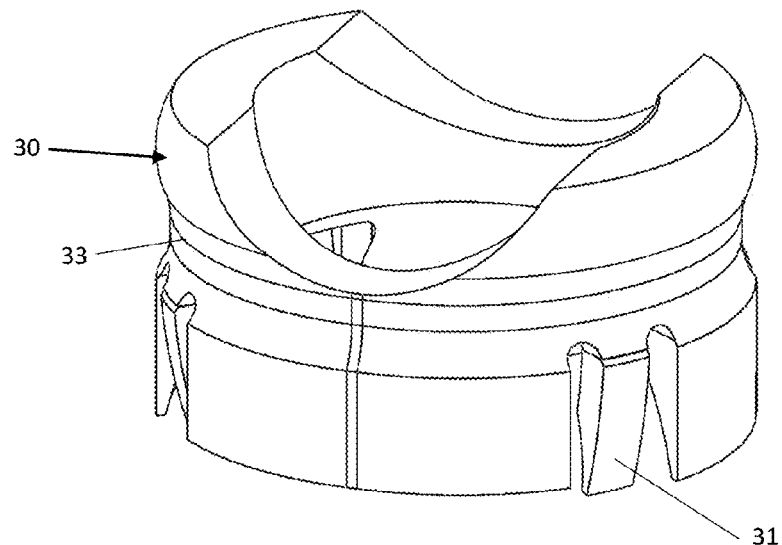
FIG. 6 is a perspective view of the saddle.
Figure 6A:
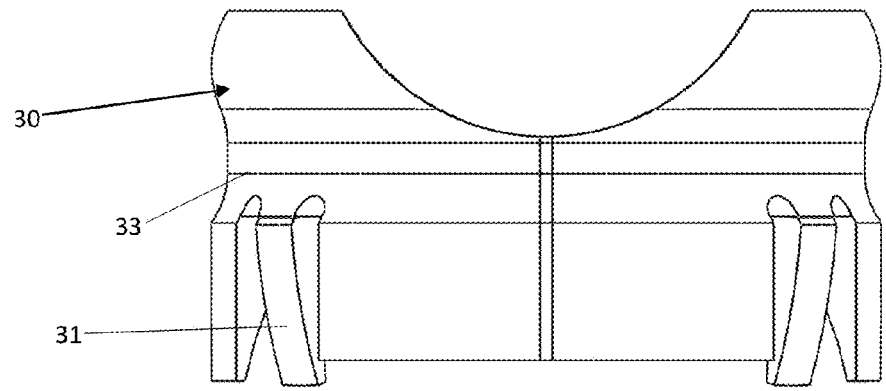
FIG. 6A is a plan view of the saddle taken from FIG. 6.

FIG. 6 is a perspective of the saddle 30 further illustrating the various elements. FIG. 6A is a plan view of the saddle 30 showing the various elements.

Figure 7:
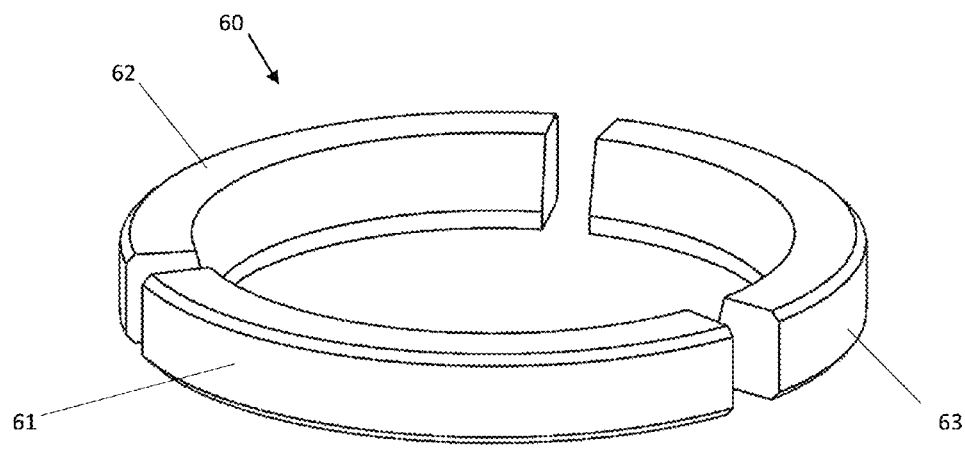
FIG. 7 is a perspective view of a plurality of arcuate locking segments aligned in an annular ring.
Figure 7A:
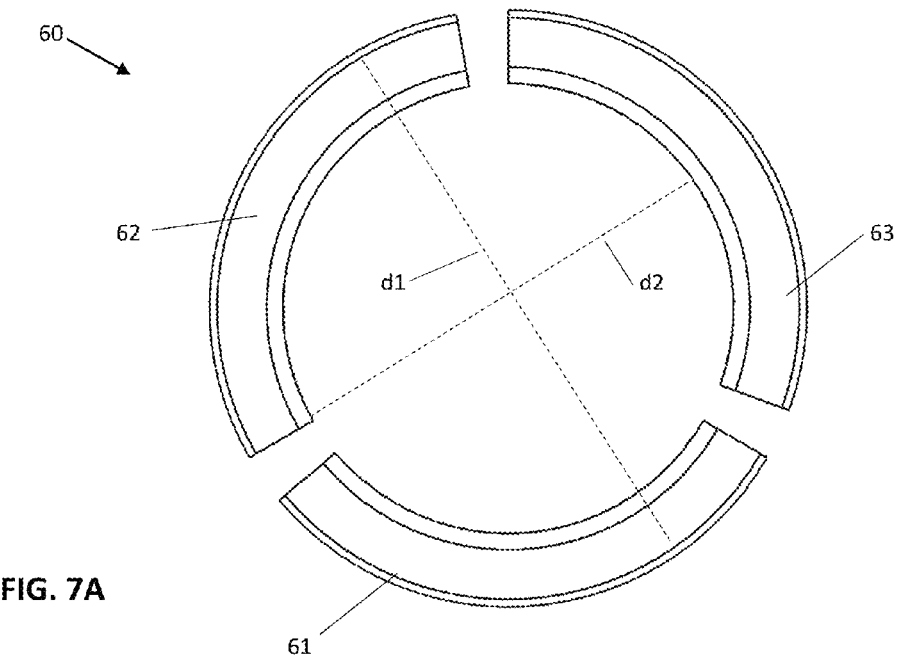
FIG. 7A is a top view of the arcuate locking segments taken from FIG. 7.

FIG. 7 shows the arcuate segments, as illustrated, 3 such arcuate segments 61, 62 and 63 are used to form the locking ring assembly 60. FIG. 7 shows the locking ring assembly having an exterior diameter d1 and an interior diameter d2, the exterior diameter d1 abuts into the recess 47 in such a way that a small gap can be created to facilitate the assembly of the bone screw 20. As indicated this can be done with two arcuate segments with two small gaps, or as shown, with three arcuate segments 61, 62, 63 with three small gaps as long as it is possible to get the segments into the recess 47 while the head 22 of the screw 20 is in position such that these segments can be slipped under the head 22 of the screw 20 to lock the screw 20 in, if so desired.

Figure 8:
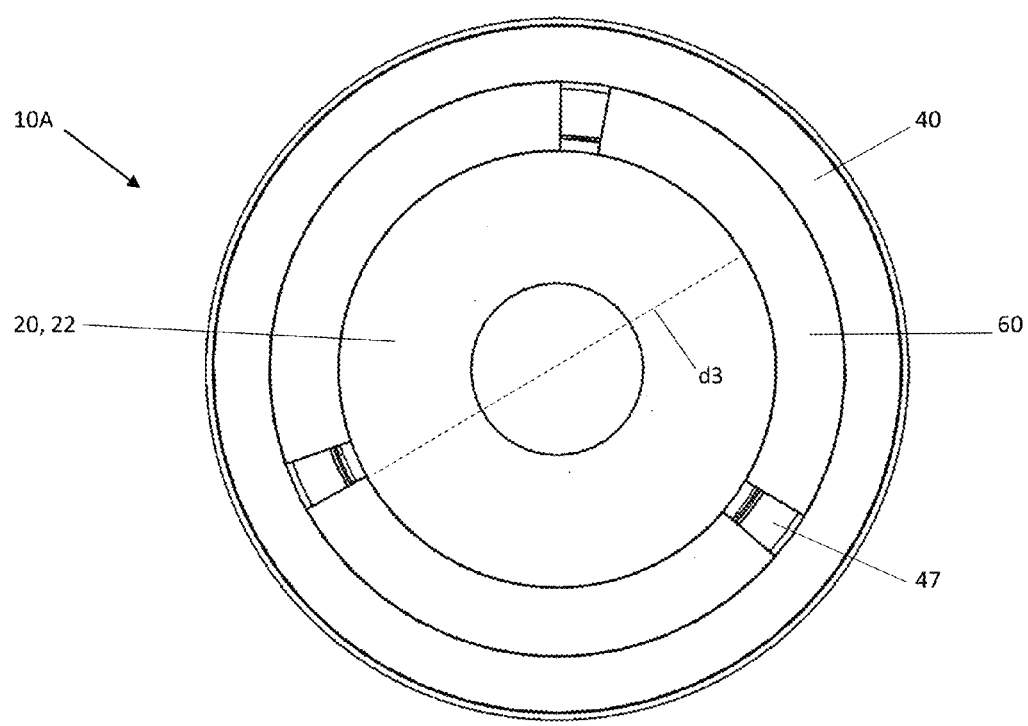
FIG. 8 is a top view of the tulip bone screw assembly of the present invention.

In this second embodiment 10A, once assembled, as shown in FIG. 8, the head 22 of the screw 20 will be positioned in such a fashion that the locking ring assembly 60 will hold the screw 20 in position as the locking segments 61, 62, 63 are positioned in the recess 47. As shown, the locking segments are sitting in the recess 47 but are protruding slightly so that the diameter d2 is smaller than the diameter d3 of the bone screw 20 at the head 22. The tulip 40 thereby can hold the bone screw head 22 from passing through the distal end 45 and lock it in position using the locking ring assembly 60. Again, when the saddle 30 is positioned in the initial loaded position with the required force to achieve the friction fit over the projections 43 wherein the recess 33 is fully engaged. The screw 20 will be free to rotate without any constraints, however, once the screw 20, locking ring and saddle 30 are assembled, a final force is provided on the exterior surface of the saddle 30 driving the saddle inwardly such that the recess 33 of the saddle 30 is moved past the projections 43 and the end of the saddle is thereby positioned below the projections 43 thereby causing the friction fingers 31 to deflect outwardly as the saddle 30 presses against the head 22 of the screw 20 thereby positioning the screw 20 firmly between the locking ring assembly 60 and the saddle 30. As before, in this second embodiment 10A, the friction fingers 31 will hold against the exterior surface of the head 22 in such a way that the bone screw 20 can be held in alignment in any position of the polyaxial head 22 as desired by the surgeon. Accordingly, the bone screw 20 can be pre-positioned to the desired location as previously mentioned.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A tulip bone screw assembly comprising;
a bone screw having a threaded shank and a polyaxial bulbous head;
a tulip having a slotted opening for receiving a rod, internal threads and an open distal end for passing the shank of the bone screw and holding the head and projections positioned between the internal threads and the distal end; and
a saddle having an axis defined by a center opening, a proximal concave end for engaging and holding the rod and a distal end with a plurality of friction fingers bent inwardly toward an axis of the saddle for applying a friction force to an exterior upper surface of the bulbous head of the bone screw, the saddle having an exterior locking surface or groove positioned between the ends, the locking surface or groove being sized to move axially inside the tulip over or past the projections fixing the saddle inside the tulip on assembly wherein the bulbous head of the bone screw is spaced between the distal end and the friction fingers on assembly wherein the bulbous head is sized to bend the friction fingers outwardly along the exterior upper surface of the bulbous head creating a friction force on the upper surface during assembly to hold the screw position relative to the axis of the tulip when the locking surface or groove is moved over the projections in a pre-loaded position and wherein the locking surface or groove of the saddle is moved distally past the projections of the tulip in a final assembly position the saddle firmly engages against the upper exterior surface of the bulbous head with a force causing the plurality of friction fingers to deflect outwardly mimicking the contour of the upper exterior surface of the bulbous head while applying a force firmly positioning the bone screw such that it will not freely move absent being physically adjusted.

2. The tulip bone screw assembly of claim 1 wherein the bulbous head of the bone screw has an at least partially hemispherical or spherical shape.

3. The tulip bone screw assembly of claim 1 wherein the bulbous head of the bone screw has a driving feature for torsionally driving the bone screw into bone.

4. The tulip bone screw assembly of claim 1 wherein the driving feature is a hexagonal or star shape opening for receiving a torque driver.

5. The tulip bone screw assembly of claim 1 wherein the plurality of friction fingers are integral to a saddle body.

6. The tulip bone screw assembly of claim 1 wherein the tulip has a recess adjacent the distal end, the recess of the tulip is configured to receive a plurality of arcuate locking ring segments.

7. The tulip bone screw assembly of claim 1 wherein the combined outer diameter of the arcuate locking ring segments is larger than a distal opening of the tulip at the distal end.

8. The tulip bone screw assembly of claim 1 wherein the bone screw has one of the following bulbous head shapes; at least partially a hemispherical or spherical head, conical or a radial array or loci of cylindrical surfaces or any other bulbous head.

9. A method of assembling a tulip comprises the step of: providing a tulip with projections; and
positioning a saddle with a concave locking surface inside the tulip over the projections inside the tulip in pre-loaded position inserting the head of the bone screw bottom loading the bone screw into the tulip to create the assembly and inserting the plurality of arcuate locking segments to fix the bone screw and then re-positioning the saddle pushing the concave locking surface past the projections inside the tulip to a final assembly position.

10. The method of assembling a tulip of claim 9 wherein the step of inserting the locking segments into the tulip and pushing the saddle against the upper exterior surface of the bone screw head bends the friction fingers on assembly to create a friction force to position a shank of the bone screw and wherein the locking surface or groove of the saddle is moved distally past the projections of the tulip in a final assembly position the saddle firmly engages against the upper exterior surface of the bulbous head with a force causing the plurality of friction fingers to deflect outwardly mimicking the contour of the upper exterior surface of the bulbous head while applying a force firmly positioning the bone screw such that it will not freely move absent being physically adjusted.

11. A rod receiving bone screw assembly comprising:
a bone screw, the bone screw having a threaded shank and polyaxial bulbous head;
a tulip, the tulip having a slotted opening for receiving a rod and internal threads inside the tulip and projections below the internal threads;
a plurality of arcuate locking segments internal of the tulip positioned in a recess of an inner surface of the tulip;
a saddle having an axis defined by a center opening, a proximal concave end for engaging and holding the rod and a distal end with a plurality of friction fingers bent toward an axis of the saddle for applying a friction force to an exterior upper surface of the bulbous head of the bone screw, the saddle having an exterior locking surface or groove positioned between the ends, the locking surface or groove being sized to move axially inside the tulip over or past the projections and fixing the saddle inside the tulip on insertion; and
after insertion of the saddle into the tulip forming the rod receiving bone screw assembly, the bone screw is positioned wherein a lower surface of the bone screw bulbous head rests against the locking ring segments and wherein in a pre-assembled unfixed position, the saddle is then moved inwardly with a proximal end past the projections and wherein the locking surface or groove of the saddle is moved distally past the projections of the tulip in a final assembly position the saddle firmly engages against the upper exterior surface of the bulbous head with a force causing the plurality of friction fingers to deflect outwardly mimicking the contour of the upper exterior surface of the bulbous head while applying a force firmly positioning the bone screw such that it will not freely move absent being physically adjusted causing the bone screw to be positioned wherein the friction fingers move proximally pressing the head of the bone screw against the locking segments causing the bone screw shank to be held frictionally but adjustably movable relative to the axis of the saddle prior to rod insertion locking the bone screw into the tulip.

12. The rod receiving bone screw assembly of claim 11 wherein the bulbous head of the bone screw has an at least partially hemispherical or spherical shape.

13. The rod receiving bone screw assembly of claim 11 wherein the bulbous head of the bone screw has a driving feature for torsionally driving the bone screw into bone.

14. The rod receiving bone screw assembly of claim 11 wherein the driving feature is a hexagonal or star shape opening for receiving a torque driver.

15. The rod receiving bone screw assembly of claim 11 wherein the friction fingers are integral to a saddle body.

16. The rod receiving bone screw assembly of claim 11 wherein the recess of the tulip is an annular groove inward of the distal end.

17. The rod receiving bone screw assembly of claim 11 wherein the outer diameter of the plurality of arcuate locking segments is larger than a distal opening of the tulip at the distal end.

18. The rod receiving bone screw assembly of claim 11 wherein the saddle is held temporarily in place by the tulip projections during initial implantation and moves away from said projections during final locking of the tulip assembly bending the locking fingers substantially back into their original pre-bent positions and compressing on the bulbous head of the bone screw.

* * * * *